United States Patent [19]

Schulz et al.

[11] Patent Number: 5,246,787
[45] Date of Patent: Sep. 21, 1993

[54] TOOL OR INSTRUMENT WITH A WEAR-RESISTANT HARD COATING FOR WORKING OR PROCESSING ORGANIC MATERIALS

[75] Inventors: Hans Schulz, Balzers, Liechtenstein; Helmut Daxinger, Wangs, Switzerland; Erich Bergmann, Mels, Switzerland; Jürgen Ramm, Flaesch, Switzerland

[73] Assignee: Balzers Aktiengesellschaft, Liechtenstein, Liechtenstein

[21] Appl. No.: 892,622

[22] Filed: Jun. 1, 1992

Related U.S. Application Data

[63] Continuation of Ser. No. 613,393, Nov. 14, 1990, abandoned.

[30] Foreign Application Priority Data

Nov. 22, 1989 [CH] Switzerland .................. 4189/89

[51] Int. Cl.$^5$ ............................. C25D 11/02
[52] U.S. Cl. .................... 428/629; 249/116; 249/135; 428/469; 428/472.2; 428/622
[58] Field of Search ............ 425/470; 428/621, 622, 428/627, 628, 629, 469, 472.2; 249/116, 134, 135; 606/167

[56] References Cited

U.S. PATENT DOCUMENTS

| | | | |
|---|---|---|---|
| 3,837,894 | 9/1974 | Tucker, Jr. | 428/627 |
| 3,890,109 | 6/1975 | Jones | 428/469 |
| 4,082,575 | 4/1978 | Eastman | 148/16.6 |
| 4,239,819 | 12/1980 | Holzl | 428/627 |
| 4,284,687 | 8/1981 | Dreyer et al. | 428/469 |
| 4,450,205 | 5/1984 | Itaba et al. | 428/627 |
| 4,526,673 | 7/1985 | Little et al. | 204/192.35 |
| 4,556,607 | 12/1985 | Sastri | 428/627 |
| 4,623,400 | 11/1986 | Japka et al. | 427/249 |
| 4,837,091 | 6/1989 | Nickola | 427/367 |
| 4,985,313 | 1/1991 | Penneck et al. | 428/629 |
| 5,075,181 | 12/1991 | Quinto et al. | 428/469 |

FOREIGN PATENT DOCUMENTS

| | | | |
|---|---|---|---|
| 0043781 | 1/1982 | European Pat. Off. | |
| 0209137 | 1/1987 | European Pat. Off. | |
| 2357321 | 2/1978 | France | 428/627 |
| 2393079 | 12/1978 | France | |
| 59-87988 | 5/1984 | Japan | 606/167 |
| 59-185773 | 10/1985 | Japan | 428/469 |
| 63-297551 | 12/1988 | Japan | |
| 63-297552 | 12/1988 | Japan | |
| 2140462A | 11/1984 | United Kingdom | 428/469 |

OTHER PUBLICATIONS

Ahmed et al., 4 EME Colloque Intern. Sur Les Plasmas et La Pulverization Sep. 13-17, 1982.

*Primary Examiner*—Jay H. Woo
*Assistant Examiner*—Robert B. Davis
*Attorney, Agent, or Firm*—Notaro & Michalos

[57] ABSTRACT

A coated tool or instrument has a wear-resistant hard coating (7) which is preferably titanium nitride for working organic material which is disposed on a separating layer (9) applied on a basic steel body (3). The separating layer (9) includes a ceramic electrically non-conducting material. Such a material is preferably an aluminum oxide or an oxide, nitride or oxynitride of silicon. The separating layer (9) protects the basic body (3) of the tool or instrument of e.g. a non-corrosion resistant steel. During the coating of the basic body (3) with the ceramic material, a pulsating dc voltage is applied to the basic body (3) or its holders. The pulse height is changed during the vapor deposition from high negative values to low negative values.

6 Claims, 1 Drawing Sheet

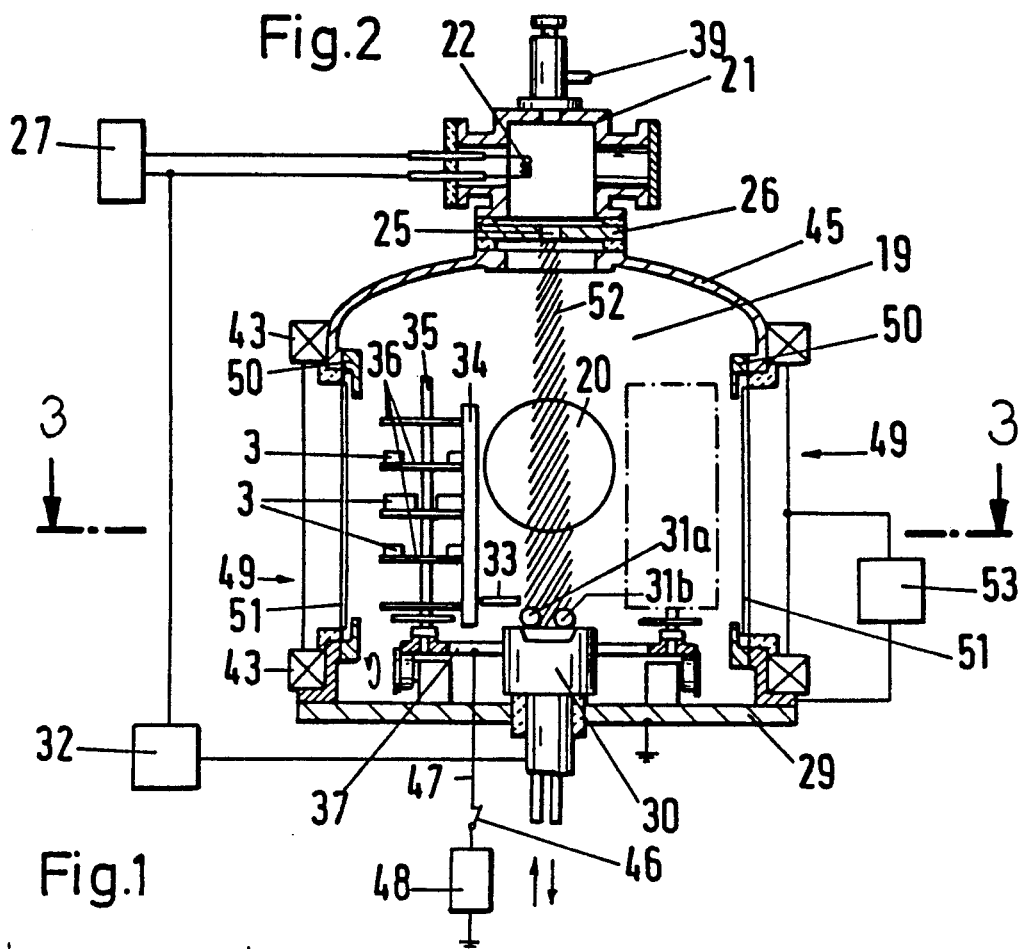
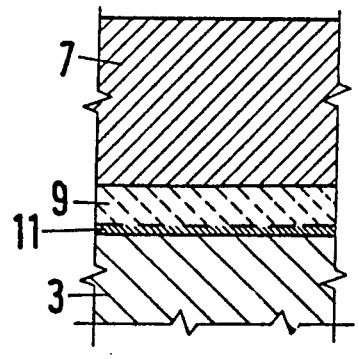
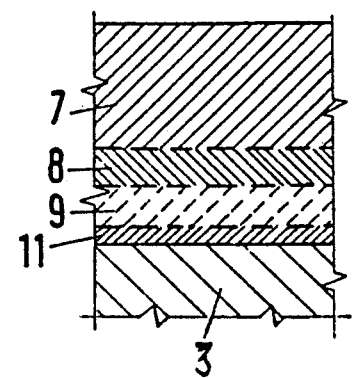
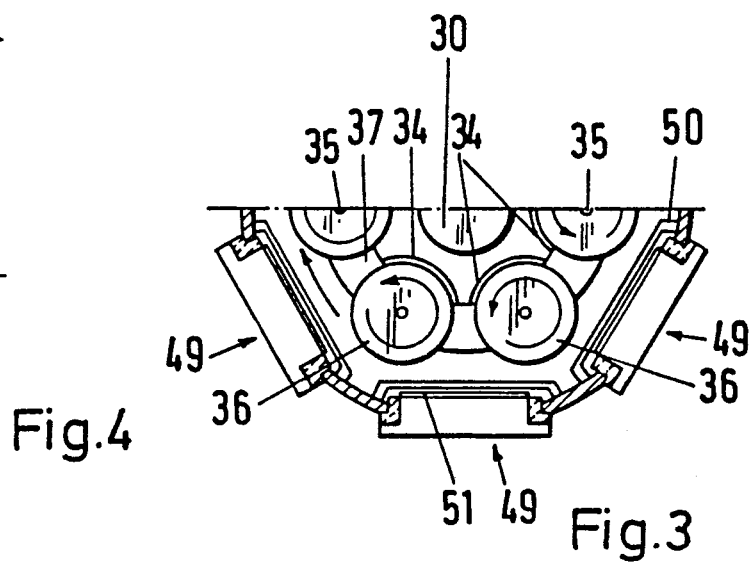

TOOL OR INSTRUMENT WITH A WEAR-RESISTANT HARD COATING FOR WORKING OR PROCESSING ORGANIC MATERIALS

This application is a continuation division, of application Ser. No. 07/613,393, filed Nov. 14, 1990 now abandoned.

FIELD AND BACKGROUND OF THE INVENTION

The present invention relates to a tool or instrument with at least one wear-resistant hard coating and to a method for the production of the coating.

The known tools and instruments for working organic materials due to their field of application require a basic body with an extremely high toughness. Steels have these characteristics; however, they are not corrosion-resistant. As a protection against corrosion the known tools and instruments were chromium-plated. This chromium layer could only temporarily protect the basic body in an aggressive environment; after only a short time it peeled off.

From German patent application DE-OS 36 39 469 a further cutting and form tool with high wear-resistance and corrosion reduction is known which has several intermediate layers and a black covering coating comprising a hard carbon coating (iC) with embedded crystallites of the carbide of the intermediate layer. The first one of the intermediate layers comprises an element of group IVb or Vb of the periodic system of elements (titanium, zirconium, hafnium, vanadium, niobium or tantalum), the second layer comprises a nitride of this element, and the third layer comprises a carbide layer of the same element.

The corrosion resistance of other known cutting and form tools is specifically deficient in the processing of organic materials inter alia in their use as vulcanization and synthetic material forms for injection moulding. A separation of the layer in the salt spray mist test already occurred after 48 hours, i.e. tools and instruments coated in such a way are not safe for multiple use in dishwashing machines and for multiple sterilization. The production method in which three intermediate layers must be applied on a basic body of the cutting and form tool furthermore is elaborate. The black to anthracite-colored surface produces visually unattractive cutting tools, e.g. for household or for surgical instruments.

SUMMARY OF THE INVENTION

The present invention is based on the task of creating a coating on a tool or instrument which is durable, multiply dishwasher-resistant or multiply sterilizable, and simple to produce, which also yields a long life with reduced abrasion even in an environment which for the basic body of the tool or instrument is aggressive and corroding, especially when used as a cutting tool for organic materials, as surgical instrument, as an instrument for manicures, pedicures etc. and a form tool for vulcanization or plastic injection-moulding forms. Moreover, an attractive color realization of the surface is to be made possible without diminishing the above stated advantageous characteristics.

Accordingly, an object of the present invention is to provide a tool for working organic materials which comprises a basic body, a separating or intermediate layer comprising ceramic, electrically non-conducting material on the basic body and a hard wear-resistant coating layer on the separating layer.

A further object of the present invention is to provide a method for producing the tool which comprises vaporizing an oxide and/or nitride former material and at least partially ionizing the same in a vacuum chamber, introducing into the vacuum chamber, a reaction gas, in particular nitrogen and/or oxygen, which is also at least partially ionized so that a ceramic separating layer is formed on a basic body as a compound of oxide and/or nitride former with the nitrogen and/or oxygen, and depositing a wear-resistant coating on the separating layer.

BRIEF DESCRIPTION OF THE DRAWINGS

In the following an example of the tool or instrument according to the invention and of the method according to the invention for coating the tool or instrument will be described in greater detail in conjunction with the drawings, wherein:

FIG. 1 is a section through a schematic representation of a coating according to the invention of a tool or instrument, FIG. 2 is a section through a vapor deposition installation represented schematically, FIG. 3 is a section through the vapor deposition installation in FIG. 2, taken along line 3—3, wherein because of axial symmetry, only one half of the vapor deposition installation is shown, and FIG. 4 is a section through a variant of the coating represented in FIG. 1.

DESCRIPTION OF THE PREFERRED EMBODIMENT

Organic materials are here meant to include materials described by organic chemistry. In particular animal and plant products as well as synthetic materials are included which are to be worked, inter alia, by vulcanization forms, synthetic injection-moulding forms, and knives, for example, for cutting meat. Implants to be used in the human body are also included.

FIG. 1 is a section that is perpendicular to the surface of the tool or instrument according to the invention. FIG. 1 shows a basic body 3 with a hard coating 7 on its outside surfaces and an intermediate separating layer 9. The separating layer 9 applied according to the method described below is radiographically amorphous, i.e. when irradiated with X-rays, it exhibits on the side of the separating layer 9 facing away from the source of the X-rays only an approximately Gaussian intensity distribution with a radiation maximum in the ray center; no far zone order (Debye-Schere diagram) can be recognized.

The hard coating 7 comprises essentially titanium nitride with a layer thickness of 3 $\mu$m.

The separating layer 9 comprises a ceramic electrically non-conducting material whose layer thickness depending on the material used and field of application is between 0.5 and 5 $\mu$m. Ceramic material here means a chemical compound known in its solid form as ceramic, wherein the structure of the separating layer 9 can also be amorphous. Aluminum oxide, $Al_2O_3$ as described below is preferably used as the ceramic material.

In a transition layer 8 shows in FIG. 4, the material of the separating layer 9 gradually changes over into the material of the hard coating 7. The separating layer 9 in the direction toward the basic body 3 also changes over gradually in a further transition layer 11 into aluminum, which is the bonding partner of the aluminum oxide of the material of the separating layer 9 as shown also in FIG. 1.

FIG. 2 is a schematic representation of an example of a vapor deposition installation for carrying out the coating according to the invention. The vapor deposition installation has a vacuum chamber 19 with an evacuation port 20 and a thermionic cathode chamber 21 connected via an opening 25 with the vacuum chamber 19. The bottom 26 of the thermionic cathode chamber 21 containing the opening 25 is electrically insulated from the walls of the vacuum chamber 19. The thermionic cathode 22 is fed by a current supply unit 27. Below the opening 25 and above the bottom 29 of the vacuum chamber 19, a crucible of titanium is positioned, in which are disposed aluminum 31a as an oxide former and titanium 31b as a nitride former. The titanium crucible, a so-called titanium liner, is placed in a coolable copper crucible. This configuration is referred to below as a crucible 30. The titanium liner ensures heat insulation relative to the copper crucible and facilitates the alloying capability of aluminum with titanium in order to favorably influence the viscosity and the reactivity in the layer process, relative to oxygen. The aluminum 31a and the titanium 31b can be covered with a slidable screen 33. Six electrically conducting supports 35 are positioned in vacuum chamber 19 and are rotatable about the longitudinal axis of the chamber. Four are illustrated in FIG. 3, each with one holder 36 that carries one or more basic bodies 3 of steel to be coated. The supports 35 are each rotatably about their own axis on a rotary table 37 and through it, are electrically connected to each other. The rotary table 37 is electrically insulated relative to the bottom 29 and the walls of the vacuum chamber 19. The holders 36 are electrically connected to the supports 35. The basic bodies 3, held on the holders 36, are coverable with a screen 34 represented schematically in FIG. 2 and 3, opposite the aluminum and titanium 31a and 31b in the crucible 30.

A gas feed line 39 terminates in cathode chamber 21 and is connected via the opening 25 with the vacuum chamber 19. One magnetic coil 43 represented schematically, is positioned just above the bottom 29 and another coil 43 is connected to a cover 45 of the vacuum chamber 19 for generating an approximately parallel vertical magnetic field.

The rotary table 37 is connected via an electrical line 47 and a closed switch 46, to a variable voltage generator 48 whose other pole is at ground.

In the vertical walls of the vacuum chamber 19 are placed six devices 49 for cathode sputtering, of which three are represented in FIG. 3. Each device 49 is provided with a heat exchanger (not shown) for cooling. Within an annulus 50 of each device 49, is positioned a target 51 which is isolated from the annulus and which is connected to the negative pole of a voltage source 53. The positive pole of the voltage source 53 is connected to the walls of the vacuum chamber 19 and to the annulus 50. The thermionic cathode 22 and the crucible 30 are connected via electrical lines to a current supply unit 32.

For the production of the coating, the basic bodies 3 are fastened on the holders 36 of the supports 35 and aluminum 31a and titanium 31b are placed in the crucible 30. Subsequently the vacuum chamber 19 is closed, evacuated to a pressure of 2 mPa (1mPa or millipascal = $10^{-3}$ N/m$^2$), and the surfaces of the objects 3 to be coated are heated to 450° C. with a low-voltage arc according to a method described in Germany DE-OS 34 06 953 or Swiss Patent CH-P 658 545, and purified according to a method described in Swiss Patent CH-P 631 743. The screen 33 covers the aluminum 31a and titanium 31b in the crucible 30 during this time.

Argon is introduced into the vacuum chamber 19 and its pressure is adjusted to 0.15 Pa. Screen 33 is removed and a low-voltage arc 52 is fired to the crucible 30. At a current of the low-voltage arc 52 of 80 A an alloying of aluminum 31a and titanium 31b takes place without any significant vaporization of the aluminum. After approximately 4 minutes this process is completed, the screen 34 in front of supports 35 is folded away and the current of the low-voltage arc 52 is increased to 120 A in order to vaporize aluminum. Due to the large differences of five orders of magnitude in the vapor pressures of aluminum and titanium, no titanium is vaporized. Within the next 4 minutes aluminum is vaporized without addition of a reactive gas and deposited directly on the surface of the basic body 3 as the lowest region of the transition layer 11.

Within the following two minutes oxygen is introduced through the gas feed line 39 with increasing quantities of flow and a total pressure in the vacuum chamber 19 of 0.4 Pa is set. The oxygen is partially ionized through the low-voltage arc 52. The partially ionized oxygen and the partially ionized aluminum combine on the surface of the basic body to form Al$_2$O$_3$ and adhere to it. Depending on the quantity of available oxygen the ratio of the deposited quantity of aluminum oxide to aluminum varies. At the above final pressure the oxygen inflow is 200 standard cm$^3$/minute. In order for the vaporization rate of the aluminum not to decrease due to its consumption through a current regulation (not shown) the current of the low-voltage arc 52 is regulated up. Within the next 15 minutes the current of the low-voltage arc 52 is regulated up to 200 A and a substantial portion of the aluminum is vaporized.

When a layer thickness of the separating layer of 1 μm has been applied, the oxygen inflow is continuously reduced at a rate at which a nitrogen inflow is continuously increased, so that the above pressure of 0.4 Pa in the vacuum chamber 19 is maintained. This process step lasts for 5 minutes and the transition layer 8 of Al$_x$Ti$_y$O$_u$N$_v$ between the separating layer 9 and the hard coating 7 still to be produced is completed, wherein the values for x and u decrease with growing transition layer 8 and the values for y and v increase. The values for v are chosen to be approximately equal to the values of y and the values of u are approximately (3/2)* x. During the following 30 minutes titanium is vaporized with the low-voltage arc 52 from the crucible 30 in the nitrogen atmosphere and the titanium nitride hard coating 7 is deposited on the transition layer 8. Subsequently the low-voltage arc 52 and the nitrogen inflow are switched off.

In place of an aluminum oxide layer Al$_2$O$_3$ a silicon nitride layer Si$_3$N$_4$ can also be applied as a separating layer 9. Herein only silicon is placed into the crucible 30. The low-voltage arc 52 is fired and burns from the thermionic cathode 22 to the silicon in the crucible 30 with an arc voltage of 90 V and a current of 60 A wherein the voltage decreases to 70 V on reaching the melting point and the current increases to 200 A due to the conductivity of the silicon which increases with the temperature.

In a subsequent process step the magnitude of the current of the low-voltage arc 52 is maintained at 200 A at an arc voltage of 70 V. In this way, the silicon from the crucible 30 is converted into the gaseous state and partially ionized.

In a second process step, nitrogen is introduced through the gas feed line 39 into the argon atmosphere which was used during a purification process (not shown). The nitrogen is partially ionized by the low-voltage arc 52. Simultaneously the screen 34 is folded away from the basic bodies 3. The partially ionized nitrogen and the partially ionized silicon combine on the surface of the basic bodies 3 to form $Si_3N_4$ and adhere to it. The basic bodies 3 rotate also during this process step.

During this second process step the partial pressure of argon is 0.4 Pa and that of the nitrogen 0.3 Pa. A pulsating dc voltage with a period of 10 $\mu s$ is applied to the supports 35. At the beginning of this process step, the voltage generator 48 supplies negative pulses with a pulse width of 8 $\mu s$ and an amplitude of $-200$ V. In the following 2 $\mu s$ the supports 35 are at ground via the voltage generator 48. During this process step the amplitude is changed toward lower negative values in such a way that toward the end they are around $-10$ V.

The material of the ceramic separating layer 9 can also be converted, into the gaseous state by an electron beam, through cathode sputtering, by plasma-enhanced vaporization or by a cathodic arc vaporization. The arc discharge, apart from the low-voltage arc, can also operate with a hot filament, with spark vaporization or with a hollow cathode.

It is also possible for the separating layer 9 to be formed of an oxide and/or nitride of an element of group IVb (titanium, zirconium, hafnium), Vb (vanadium, niobium, tantalum), VIb (chromium, molybdenum, tungsten) or of a mixture of these substances or mixtures of these substances with an oxide, nitride or oxynitride of aluminum.

Instead of grounding the pole of the voltage generator 48 which not connected to line 47, this pole can also be connected to the crucible 30 or to the anode potential of the low-voltage arc 52. Instead of changing the pulse height from $-200$ V to $-10$ V, the pulse width can also be decreased; it is also possible to change the pulse height and the pulse width.

Instead of applying the hard coating 7 by ion plating it can also be sputtered on. To this end targets 51 are formed of titanium; in this case only silicon is placed in the crucible 30. If a layer thickness of the separating layer 9 of 1 $\mu m$ is applied the silicon disposed in the crucible 30 is covered, the low-voltage arc 52 and the voltage generator 48 are switched off, the switch 46 is opened and the nitrogen inflow is adjusted to 250 standard cm$^3$ per minute. Argon is introduced into the vacuum chamber 19 until a pressure of 0.8 Pa is reached. A voltage of 650 V is applied to the target 51 (size 5 $\times$ 18 inches) with the voltage source 53 whereby a sputtering power of 10 kW per target 51 is obtained. A dc voltage of $-80$ V is applied to the basic bodies 3. The nitrogen inflow is controlled in such a way that no target poisoning takes place. If within one half hour a titanium nitride layer thickness of 2 $\mu m$ is deposited on the separating layer 9, the voltage source 53 is switched off. The vacuum chamber 19 is vented and subsequently opened to remove the coated workpieces or instruments.

For generally known applications the layer thickness of the hard coating 7 is about two to ten times that of the separating layer 9.

Instead of titanium nitride other materials can also be used as a hard coating 7 which comprise essentially compounds of nitrogen, carbon or boron with a metals of group IVb (titanium, zirconium, hafnium), Vb (vanadium, niobium, tantalum) or VIb (chromium, molybdenum, tungsten) or silicon carbide or mixtures thereof or titanium nitride and/or titanium carbon nitride.

Depending on the materials used, apart from sputtering, other PVD methods such as, for example, reactive PVD are also used for applying the hard coating.

Because of the low temperatures to which the basic body 3 is exposed during the entire coating process, heat treatments of the basic body 3 can be carried out before the coating process without running the danger of deformation.

With the basic bodies 3 coated according to the invention the ceramic separating layer drastically increases specifically the corrosion resistance. This result is surprising specifically since until now in layers applied by means of PVD "pin holes" were observed which counteract corrosion resistance.

The tool or instrument according to the invention, due to its excellent corrosion resistance and due to its high abrasion resistance, is suitable in particular for use as cutting tools for organic products and synthetic materials, as surgical instruments, as implants in the human body, as instruments for manicures, pedicures etc. as well as for form tools for vulcanization or synthetic material injection-moulding forms.

We claim:

1. A tool for working organic materials, comprising:
   a basic body of steel;
   an intermediate layer formed of an electrically non-conducting ceramic material, on the basic body, the intermediate layer being amorphous and being an oxide of aluminum; and
   a wear resistant hard coating having a Vickers hardness greater than 1500, on the intermediate layer, said hard coating forming the outside surface of the tool.

2. A tool as stated in claim 1, wherein the intermediate layer has a layer thickness of approximately 0.5 to 5 $\mu m$.

3. A tool as stated in claim 1, wherein the hard coating is titanium nitride and has two to ten times the thickness of the intermediate layer.

4. A tool according to claim 2, wherein the hard coating is titanium nitride and has two to ten times the thickness of the intermediate layer, the intermediate layer being relatively soft compared to the hard coating and being amorphous aluminum oxide which is free of pin holes and is corrosion resistant for use in a tool for organic materials.

5. A tool for working organic materials, comprising:
   a basic body of steel;
   an intermediate layer formed of an electrically non-conducting ceramic material, on the basic body, the intermediate layer being amorphous and being aluminum oxide;
   a wear-resistant hard coating of a Vickers hardness greater than 1500 on the intermediate layer, said hard coating forming the outside surface of the tool; and
   a transition layer formed by material deposited directly onto the basic body, the material being the aluminum of the intermediate layer, a material composition of the transistion layer gradually changing from aluminum at the surface of the basic body, into the aluminum oxide of the intermediate layer.

6. A tool for working organic materials, comprising:
a basic body of steel;
an intermediate layer formed of an electrically non-conducting ceramic material, on the basic body the intermediate layer being amorphous aluminum oxide and
a wear-resistant hard coating of a Vickers hardness greater than 1500 on the separating layer, said hard coating forming the outside surface of the tool, the intermediate layer being formed directly on the surface of the basic body of the tool and the hard coating being formed directly on the intermediate layer.

* * * * *